US00PP11653P

United States Patent [19]

Vlielander

[11] Patent Number: Plant 11,653

[45] Date of Patent: Nov. 28, 2000

[54] KALANCHOE PLANT NAMED 'PABLO'

[75] Inventor: Ike Vlielander, De Lier, Netherlands

[73] Assignee: Fides Beheer B.V., De Lier, Netherlands

[21] Appl. No.: 09/233,139

[22] Filed: Jan. 19, 1999

[51] Int. Cl.[7] ..... A01H 5/00

[52] U.S. Cl. ..... Plt./335

[58] Field of Search ..... Plt./339, 335, 337, Plt./341

*Primary Examiner*—Howard J. Locker
*Assistant Examiner*—Kent L. Bell
*Attorney, Agent, or Firm*—C. A. Whealy

[57] ABSTRACT

A distinct cultivar of Kalanchoe plant named 'Pablo', characterized by its unique pink and light pink bi-colored petal color; moderately vigorous plant growth habit; rapid growth rate; freely branching habit with shoots forming at every node; dark green leaves; proportional leaf size to plant size; suitable for various container sizes from 10 to 12 cm; uniform plant habit and inflorescence display; freely flowering with numerous flowers per plant; and excellent post-production longevity with plants maintaining good flower color and substance for about five to seven weeks.

1 Drawing Sheet

BACKGROUND OF THE INVENTION

The present invention relates to a new and distinct cultivar of Kalanchoe plant, botanically known as *Kalanchoe blossfeldiana* Adans., and hereinafter referred to by the cultivar name 'Pablo'.

The new Kalanchoe is a naturally-occurring whole plant mutation of the *Kalanchoe blossfeldiana* Adans. cultivar 'Kerinci', disclosed in U.S. Plant Pat. No. 10,031. The new Kalanchoe was discovered by the Inventor in a controlled environment in De Lier, The Netherlands, within a population of plants of the cultivar Kerinci. The selection of this plant was based on its unique pink and light pink bi-colored petal color.

Asexual reproduction of the new Kalanchoe by terminal cuttings taken at De Lier, The Netherlands, has shown that the unique features of this new Kalanchoe are stable and reproduced true to type in successive generations.

BRIEF SUMMARY OF THE INVENTION

Plants of the cultivar 'Pablo' have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Pablo'. These characteristics in combination distinguish 'Pablo' as a new and distinct cultivar:

1. Unique pink and light pink bi-colored petal color.
2. Moderately vigorous plant growth habit.
3. Rapid growth rate.
4. Freely branching habit with shoots forming at every node. Plants do not require pinching.
5. Dark green leaves.
6. Proportional leaf size to plant size.
7. Suitable for various container sizes from 10 to 12 cm.
8. Uniform plant habit and inflorescence display.
9. Freely flowering with numerous flowers per plant.
10. Excellent postproduction longevity with plants maintaining good flower color and substance for about five to seven weeks.

Plants of the cultivar 'Pablo' are similar to plants of the mutation parent, the cultivar 'Kerinci', in all horticultural characteristics with the exception of petal color. Plants of the cultivar 'Kerinci' have pink-colored petals whereas plants of the new Kalanchoe have pink and light pink bi-colored petals.

DESCRIPTION OF THE PHOTOGRAPH

The accompanying colored photograph illustrates the overall appearance of the new Kalanchoe, showing the colors as true as it is reasonably possible to obtain in colored reproductions of this type. The photograph comprises a top perspective view of a typical potted plant of 'Pablo' taken under natural light conditions at approximately noon in De Lier, The Netherlands. Flower and foliage colors in the photograph may appear different from the actual colors due to light reflectance.

DETAILED BOTANICAL DESCRIPTION

In the following description, color references are made to The Royal Horticultural Society Colour Chart except where general terms of ordinary dictionary significance are used. The following observations, measurements and comparisons describe plants grown in De Lier, The Netherlands, from December to April under commercial practice in a glass-covered greenhouse with day temperatures ranging from 19 to 21° C. and night temperatures of 18 to 19° C. Light levels were maintained between 10,000 to 55,000 lux using assimilation lights and shading. Plants were exposed to four weeks of long day/short nights followed by eight weeks of short day/long night photoperiodic treatments and treated with daminozide growth retardant at a rate of 4 grams per liter. Measurements and numerical values represent averages for typical plants grown in 10.5-cm containers.

Botanical classification: *Kalanchoe blossfeldiana* Adans. cultivar 'Pablo'.

Parentage: Naturally-occurring whole plant mutation of *Kalanchoe blossfeldiana* Adans. cultivar 'Kerinci', disclosed in U.S. Plant Pat. No. 10,031.

Propagation:

*Type cutting.*—Terminal cuttings.

*Time to initiate roots.*—12 days at 21° C. soil temperature.

*Rooting habit.*—Numerous, fine, fibrous, and well-branched.

Plant description:

*Form.*—Upright and uniform. Plant shape is an inverted triangle with a rounded apex. Actual plant shape will depend on whether or not plants are pinched (vegetative terminals removed).

*Branching habit.*—Freely branching, generally shoots formed at every node. Typically 6 to 7 lateral branches will develop.

*Plant height at flowering.*—About 22 cm from soil level to top of plant, appropriate for 10 to 12-cm containers.

*Lateral branch length.*—About 19 cm.

*Vigor.*—Moderately vigorous.

*Growth rate.*—Rapid.

*Crop time.*—Depending on temperature and light level, three to four weeks of long day/short night conditions followed by 7.5 to 11 weeks of short day/long night conditions for a total of 10.5 to 15 weeks are required to produce flowering plants with four to seven open flowers per plant.

*Foliage description.*—Leaves simple, opposite, generally symmetrical. Quantity: Typically about 10 to 15 mature leaves and about 16 to 25 generative leaves per plant. Length: About 11.5 cm. Width: About 8 cm. Petiole length: About 1.6 cm. Shape: Elliptic. Apex: Acute to obtuse. Base: Acute. Margin: Crenate, vaulted. Texture: Leathery, glabrous, coriaceous and succulent. A wart-like structure is typically observed on the upper leaf surface close to the leaf base. Color: Young foliage, upper surface: 137A. Young foliage, lower surface: 137B. Mature foliage, upper surface: 137A. Mature foliage, lower surface: 137B. Petiole: 137A. Venation, upper surface : 137A to 137B. Venation, lower surface: 137B.

Flower description:

*Flower type and habit.*—Single flowers arranged in compound dichasial cymes on strong peduncles. Inflorescences borne above the foliage, arising from leaf axils. Uniform inflorescence display. Freely flowering and very floriferous.

*Natural flowering season.*—Autumn/winter in the Northern Hemisphere. At other times of the year flower initiation and development can be induced under controlled photoperiods (short day/long night conditions). Opening of new buds will continue for at least seven weeks.

*Time to flower.*—Under warm growing temperatures, about 25° C., plants of the new Kalanchoe will start flowering after about 7.5 weeks of exposure to controlled photoperiods (short day/long night conditions). Under cooler growing temperatures, about 20° C., plants of the cultivar 'Pablo' will flower after about 11 weeks of exposure to controlled photoperiods. First flower open is the terminal flower at the main axis and is followed by the opening of the terminal flowers of the lateral branches of the inflorescence.

*Postproduction longevity.*—Plants will maintain good color and substance for about five to seven weeks depending on environmental conditions. Individual flowers last about 17 days after opening. Flowers persistent.

*Fragrance.*—None.

*Flower diameter.*—About 1.7 cm.

*Flower depth* (*height*).—About 1.4 cm.

*Quantity.*—Typically more than 200 flowers per plant.

*Flower buds.*—Length: About 9 mm. Width: About 2.5 mm. Shape: Oblong becoming tubular/ovoid with development. Rate of opening: Relatively rapid. Color: Sepals, initially 138C; petals, 49D just before opening.

*Petals.*—Quantity: Four forming a bell-shaped corolla. Length: About 8 mm. Width: About 5 mm. Shape: Ovate. Apex: Acute. Margin: Entire. Texture: Glabrous, smooth, shiny and satiny. Aspect: Flat to somewhat upright. Color: When opening: Pink, 52B, at base and center surrounded by lighter pink, 62C, at margin and apex. Mature, upper surface: Pink, 61D, at base and center surrounded by lighter pink, 62D, at margin and apex. Mature, lower surface: 49D to 50D. Fading to: Pink, 62A to 62B, at base and center surrounded by lighter pink, 56D, at margin and apex.

*Sepals.*—Quantity: Four. Shape: Oblong, pointed. Apex: Acute. Margin: Entire. Texture: Glabrous and shiny. Aspect: Upright, rigid. Color, upper and lower surfaces: 138D.

*Calyx.*—Size: About 9 mm. Shape: Funnel. Texture: Glabrous. Color: 138D.

*Peduncle.*—Length: About 4 mm. Texture: Glabrous. Aspect: Strong, rigid, and upright. Color: 138B.

*Reproductive organs.*—Stamens: Stamen number: Eight. Anther size: About 0.3 mm. Anther shape: Flat, elliptic. Anther color: Close to 150D. Pollen color: Close to 12A. Pistils: Pistil number: Four. Stigma shape: Flat. Stigma appearance: Crystalline. Stigma color: 8D. Style length: About 8 mm. Style color: 138D. Ovary number: Four-celled. Ovary color: Green.

Disease resistance: Resistance to known Kalanchoe pathogens has not been observed.

Seed production: Seed production has not been observed.

It is claimed:

1. A new and distinct cultivar of Kalanchoe plant named 'Pablo', as illustrated and described.

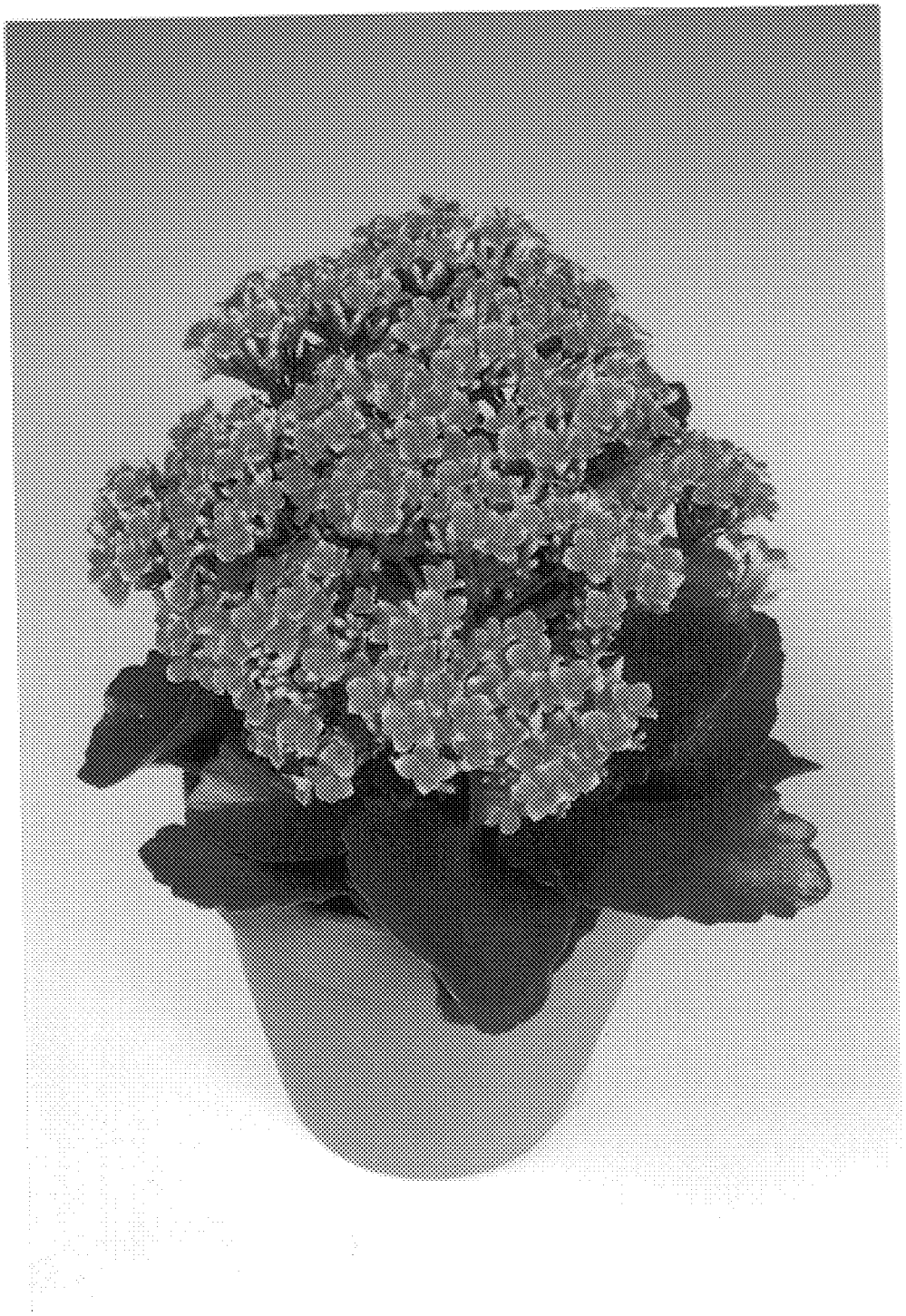

* * * * *